(12) United States Patent
Ozeki

(10) Patent No.: US 6,482,420 B2
(45) Date of Patent: Nov. 19, 2002

(54) COMPOSITION HAVING BACTERICIDAL ACTION, COSMETICS CONTAINING SAID COMPOSITION AND ULTRAVIOLET RAY SCREENING AGENT

(75) Inventor: Hiroshi Ozeki, Koshigaya (JP)

(73) Assignees: Noboru Huziwara, Tokyo (JP); Takeshi Yamazaki, Urawa (JP); Yuko Sato, Saitama (JP)

( * ) Notice: Subject to any disclaimer, the term of this patent is extended or adjusted under 35 U.S.C. 154(b) by 0 days.

(21) Appl. No.: 09/747,972

(22) Filed: Dec. 27, 2000

(65) Prior Publication Data

US 2002/0122779 A1 Sep. 5, 2002

(51) Int. Cl.⁷ ................................. A61K 7/00
(52) U.S. Cl. .................. 424/401; 924/59; 924/520; 924/538
(58) Field of Search .................. 424/59, 401, 520, 424/538

(56) References Cited

U.S. PATENT DOCUMENTS 5,882,666 A  *  3/1999  Averill et al. ............... 424/401
5,904,917 A  *  5/1999  Mattai et al. ................ 424/59

FOREIGN PATENT DOCUMENTS

| CN | 1091278 A | * | 8/1994 |
| JP | 58-26809 |   | 2/1983 |
| JP | 4-346936 |   | 12/1992 |
| JP | 5-163132 |   | 6/1993 |
| JP | 6-70702 |   | 3/1994 |
| JP | 6-321768 |   | 11/1994 |
| JP | 7-330621 |   | 12/1995 |
| JP | 8-19372 |   | 1/1996 |
| JP | 10-140154 |   | 5/1998 |
| JP | 10-158177 |   | 6/1998 |
| JP | 10-265403 |   | 10/1998 |
| JP | 11-49659 |   | 2/1999 |
| JP | 11-139986 |   | 5/1999 |

OTHER PUBLICATIONS

*FJ Fragrance Journal 84* (The magazine of research and development of raw materials for cosmetics, toiletries & allied industries); Tokyo, Japan; vol. 15, No. 3, pps. 54–58.

* cited by examiner

Primary Examiner—José G. Dees
Assistant Examiner—Konata M. George
(74) Attorney, Agent, or Firm—Armstrong, Westerman & Hattori LLP

(57) ABSTRACT

A composition having a bactericidal action is provided which has no toxicity to the human body, and particularly a composition having a bactericidal action is provided which exhibit an excellent therapeutic effect for skin diseases such as atopic dermatitis, acne or the like.

A composition, in which an extract from a silk gland and/or a liquid silk is an active ingredient, has a bactericidal action to make renewal of a skin cell, exhibiting an excellent therapeutic effect for skin diseases.

7 Claims, No Drawings

COMPOSITION HAVING BACTERICIDAL ACTION, COSMETICS CONTAINING SAID COMPOSITION AND ULTRAVIOLET RAY SCREENING AGENT

BACKGROUND OF THE INVENTION

1. Field of the Invention

This invention relates to a composition having a bactericidal action having an excellent effect on beauty and health for a skin or the like, a cosmetics containing the composition, and a ultraviolet ray screening agent.

2. Related Art

It has been well known that a vitamin, a Chinese milk vetch, hyaluronic acid, and other various additives are added into a skin cosmetics in order to maintain a healthy physical function of the skin and to maintain a healthy clear skin.

A medicinal cosmetics has been also proposed, in which where it is coated, as a medicine for external application, on the skin directly, function of the skin is activated to help regeneration of the skin.

However, no cosmetics or medicine has been heretofore known to completely recover atopic dermatitis, acne and the like in a short period of time.

On the other hand, silk has been used as raw material for high class clothes. It has been known that when a silk underwear is worn, the effect of a medicine to some extent is obtained.

However, whether an ingredient having what effect of a medicine is contained in silk, and isolation of an ingredient having the effect of a medicine have not at all been heretofore known.

Further, a number of substances having a bactericidal action have been heretofore known, but most of these were every poisonous to the human body. As a sterilizer free from toxicity to the human body, "garlic" is known, but there has been posed a problem that "garlic" gives out a very bad smell.

On the other hand, there have been known pupa oil from a cocoon and nutriment for the skin or medicinal cream containing in a cocoon extract. However, these conventional pupa oil and medicinal cream have no bactericidal action.

SUMMARY OF THE INVENTION

It is an object of this invention to provide a composition having a bactericidal action free from toxicity to the human body.

It is a further object of this invention to provide a composition having a bactericidal action which has an excellent effect particularly on skin diseases such as atopic dermatitis, acne and the like.

It is another object of this invention to provide a composition having a bactericidal action which makes renewal of the surface of the skin active, prevents decline of the skin, makes the skin smooth, and makes a birthmark and pigment unnoticeable.

It is still another object of this invention to provide a ultraviolet ray screening agent having a bactericidal action which is free from toxicity to the human body, and has an excellent effect on skin diseases.

For achieving the aforementioned object, the present inventor has found, as a result of earnest study, that water or organic solvent extract from a silk gland and/or liquid silk exhibits an excellent bactericidal action, has a great effect on treatment and improvement of atopic dermatitis, acne and skin chap, makes renewal of the surface of the skin active, prevents decline of the skin, makes the skin smooth, and has an excellent ultraviolet inhibiting action, thus arriving at the present invention.

That is, according to the feature of the present invention, an extract from a silk gland and/or liquid silk is an active ingredient which has a bactericidal action.

The above and other objects and advantages of the invention will become more apparent from the following description.

DETAILED DESCRIPTION OF THE PREFERRED EMBODIMENT

The embodiments of the present invention will be described hereinafter.

Raw materials used in the present invention include a silk gland and/or liquid silk, preferably a silk gland in the state having the liquid silk received therein. For reducing the cost of raw materials, a silk filament, a cocoon, raw silk produced from a cocoon, silk, and a pupa of silkworm can be used jointly with the aforementioned raw materials. These raw materials jointly used with the cocoon and the like are preferably used by being cut minutely or powdered in order to enhance the extraction effect.

The contents of the silk gland and/or liquid silk in the raw materials of the present invention are not less than 5%, preferably, 10% to 50%. If the contents are too little, the bactericidal action is insufficient, whereas if too much, there is less advantage despite high cost of raw materials.

There are many kinds of silkworms used to produce the raw materials. Any kind of silkworms can be used as the raw materials in the present invention. However, preferably, silkworms of 3 instar to 5 instar, 4, 5 days, particularly, immediately before spitting out the silk filament (5 instar to 5 instar, 4, 5 days) are used. Because the liquid silk in the silk gland is gelled, which is effective particularly as raw material in the present invention.

Where the silk gland having the liquid silk received therein is taken out of the silkworms immediately before spitting out the silk thread, which are not used immediately, they may be frozen rapidly and preserved. If doing so, the effective ingredients are not changed in quality.

By extracting them from the raw materials with water or organic solvents, the effective ingredients of the present invention can be isolated. As the organic solvents, preferably, use is made of alcohols, more preferably, ethyl alcohol because the latter is free from toxicity.

An extraction temperature may be a normal temperature, but heat-extraction is preferable for enhancing the extraction effect in a short period of time.

The active ingredients of the present invention are obtained by extracting the silk gland and/or liquid silk under the boiling adding water or organic solvent, and concentrating and drying a filtrate.

The thus obtained active ingredients of the present invention have the bactericidal action and exhibit the excellent effect for symptoms noted below:

(Atopic dermatitis and Sensitive Skin)

The active ingredients of the present invention exhibit, because of their antiallergic effect, the excellent effect for atopic dermatitis, and allergic dermatitis (sensitive skin) such as the hand chap, eczema, skin eruptions or the like caused by synthetic detergent.

(Pollen Disease and Cataract)

For the pollen diseases such as rhinitis and eye-itch, if the ingredient is rubbed into the affected part directly, the part is recovered completely in a short period of time. Also with respect to the cataract, if the ingredient is rubbed into the affected part directly, the part gets better in a short period of time.

(Mother's Mark and Pigment)

Since the active ingredient of the present invention promotes renewal of the skin, if the ingredient is rubbed into the mother's mark and pigment, they are inconspicuous in a short period of time.

(Dried Skin)

The active ingredients of the present invention exhibit an improvement in skin caused by renewal and an immediate effect for killing itch, with respect to the itch caused by the dried skin in a winter season.

(Chaps, Crack, Cut, Burn, Abrasion, Frostbite, Bedsore)

The active ingredients of the present invention may be rubbed into the affected part directly, but more effectively, the ingredient is coated on gauze, which is placed on the affected part.

(Skin Diseases Such as Prick, Acne, Eczema, Water Insect, Ringworm, Wart, and Insect Bite)

The renewal of the affected part becomes active by the function of the effective ingredients according to the present invention, and if the ingredient is rubbed into the affected part, the itch is killed immediately to get better.

(Pile and Hypertrophy of Prostate)

The ingredient is effective when the affected part such as periproctits is closer to the outside, and if the ingredient is rubbed into the affected par, it gets better immediately.

(Stomatitis and Alveolar Pyorrhea)

Since the active ingredients of the present invention has the bactericidal action but has no toxicity relative to the human body, the oral diseases are recovered safely and in a short period of time.

(Osmidrosis)

The active ingredients of the present invention are rubbed into the affected part to thereby make the renewal of the skin active and improve habitus. Therefore, the affected part gets better immediately.

(Plication and Wrinkles)

The ingredients of the present invention are rubbed into the wrinkle portion, whereby the wrinkles are inconspicuous and the skin becomes smooth.

The ingredients of the present invention are added to the cosmetic base material to thereby obtain the cosmetics of the present invention. The cosmetic base material is not particularly limited if the former is well known.

The forms of the cosmetics used in the present invention are not particularly limited, and include those, for example, such as cream, lotion, pack, foundation shampoo, rinse, hair tonic, bath agents and soap.

The amount of the active ingredients of the present invention added to the cosmetic base material can be varied widely, but preferably, for example, the concentrate with the solvent removed of about 0.1 to 25 weight percent is preferably added.

It has been assured according to the experiments that also with respect to the thus obtained cosmetics, the effect of a medicine similar to the aforementioned effective ingredients is obtained.

The active ingredients of the present invention has a ultraviolet inhibiting action. Accordingly, if the active ingredients of the present invention of about 0.1 to 25 weight percent is added as the concentrate to the cosmetic base material, the same ultraviolet inhibiting action as anti-suntan cream is obtained without adding a ultraviolet absorbent particularly. The effective ingredients of the present invention further has an action for dissolving a melanine coloring matter. Accordingly, if the cream of the present invention is applied to the suntan skin, the action for whitening the skin also exhibits as well as the anti-suntan action.

The active ingredients of the extract from raw materials comprising one or more kinds of silk gland and/or liquid silk, silk filament, cocoon, raw silk, silk and pupa of silkworm, containing no silk gland and/or liquid silk also has the ultraviolet inhibiting action. This is, however, inferior in effect to the effective ingredients of the present invention.

Examples of the present invention are shown below, but the present invention is not limited thereto. In the Examples, "part" representing the quantities indicates "weight part".

EXAMPLE 1

200 parts of water were added to 20 parts of silk glands (liquid silk is accommodated) and 200 parts of cocoons, which were boiled for 3 hours. Then, they are filtrated, and a filtrate was reduced and concentrated. 50 parts of the active ingredients of the present invention were obtained as a concentrated and dried light yellow liquid.

EXAMPLE 2

Cream

| Active ingredients obtained in Example 1 | 13 parts |
|---|---|
| Ethanol | 5 parts |
| Beeswax | 6 parts |
| Squalene | 20 parts |
| Fatty acid glycerine | 4 parts |
| Emulsifier | 4 part |
| 1,3-butylene glycol | 3 parts |
| Alpha bisaborol (Eiko 101) | 0.3 part |
| Refined water | 44.7 parts |

The above ingredients are uniformly mixed in the ratio as described above to obtain the cream of the present invention.

EXAMPLE 3

Hair Tonic

| Active ingredients obtained in Example 1 | 10 parts |
|---|---|
| Ethanol | 55.3 parts |
| Menthol | 4.4 parts |
| Alpha bisaborol (Eiko 101) | 0.3 part |
| Refined water | 34.3 parts |

The above ingredients are uniformly mixed in the ratio as described above to obtain the hair tonic of the present invention.

EXAMPLE 4

Shampoo

| Active ingredients obtained in Example 1 | 10 parts |
|---|---|
| N-coconut oil fatty acid acyl-L-glutamic acid monotriethanol amine | 26.0 parts |
| Alpha bisaborol (Eiko 101) | 0.5 part |
| Laurylether sodium sulfate | 29.0 parts |
| Propylene glycol | 2.0 parts |
| Refined water | 37.5 parts |

The above ingredients are uniformly mixed in the ratio as described above to obtain the shampoo of the present invention.

EXAMPLE 5
Medical Effect for Atopic Dermatitis

Testees are three women suffering from that the condition of the skin is apparently atopic dermatitis from an external appearance. The cream obtained in Example 1 was rubbed into the face while diluting it in a small amount, in a normal using amount once a day, progress of which was observed with naked eye. The results are given in the following Table 1.

TABLE 1

| | | | Passage | | |
|---|---|---|---|---|---|
| Testee No. | Age | Occupation | 1 week | 1 month | 3 months |
| 1 | 15 | Student | + | O | |
| 2 | 18 | Student | ± | O | |
| 3 | 35 | OL | ± | + | O |

Where, ± . . . Condition of a disease was improved as compared with the condition before use.
+ . . . Condition of a disease became inconspicuous.
O . . . Completely recovered to the normal state As will be apparent from the above-described results, when the cosmetics of the present invention is used, the condition of atopic dermatitis is improved in a week, and is completely recovered at least in 3 months.

EXAMPLE 6
Medical Effect for Acne

Testees are five women suffering from that the condition of the skin is apparently acne from an external appearance. The cream obtained in Example 1 was rubbed into the face while it in a small amount, in a normal using amount once a day progress of which was observed with naked eye. The results are given in the following Table 2.

TABLE 2

| | | | Passage | | |
|---|---|---|---|---|---|
| Testee No. | Age | Occupation | 1 week | 1 month | 3 months |
| 1 | 13 | Student | ± | O | |
| 2 | 15 | Student | ± | O | |
| 3 | 18 | Student | ± | + | O |
| 4 | 21 | OL | ± | O | |
| 5 | 22 | OL | ± | + | O |

Where, ± . . . Acne became small as compared with the condition before use.
+ . . . Condition of a disease became inconspicuous.
O . . . Completely recovered to the normal state Where, ± . . . A Acne became small as compared with the condition before use.

+ . . . Condition of a disease became inconspicuous.

O . . . Completely recovered to the normal state

As will be apparent from the above-described results, when the cosmetics of the present invention is used, the condition of acne is improved in a week, and is completely recovered at least in 3 months.

EXAMPLE 7
Medical Effect for Various Conditions of a Disease

The cream obtained in Example 1 was rubbed into the testees suffering from the conditions of a disease described in Table 3 while diluting it in a small amount, in a normal using amount once a day, progress of which was observed with naked eye, The results are given in the following Table 3.

TABLE 3

| Disease | Passage |
|---|---|
| Mother's mark | Mother's mark became small, and became inconspicuous in 3 months |
| Bedsore | Pain was softened immediately, and was completely recovered in a month. |
| Pollen disease | Itch was stopped immediately, and was completely recovered in a month. |
| Water insect | Itch was softened immediately, and was completely recovered in a month. |
| Pile | Pain was softened immediately, and was completely recovered in a month. |
| Stomatitis | Pain was softened immediately, and was completely recovered in a month. |
| Cataract | Effect was taken in a few days, and was completely recovered in a month. |
| Wrinkles | Became inconspicuous in a week, and the skin became Smooth. |

As will be apparent from the above-described results, when the cosmetics of the present invention is applied, pain and itch are softened immediately, and even the condition of disease which is hard to be completely recovered such as mother's mark can be completely recovered at least after passage of 3 months.

EXAMPLE 8
Cream having Only Raw Silk as Raw Material was Compared with Cream Containing Silk Gland as Raw Material The Odor and Feel between the cream of the present invention and the comparative cream were compared (A) Cream having only raw silk as raw material: Comparative cream was produced in a manner similar to Example 1 except that 300 parts of raw silk were used in place of 20 parts of silk glands and 200 parts of cocoons.

(B) Cream containing silk gland as raw material: Cream of the present invention was produced in a manner similar to Example 1.

(1) Odor: In case of only raw silk, odor peculiar to raw silk remains unless spices is used, but in case of silk gland used as main ingredient, when the cream is rubbed into the skin thinly, it permeates into the skin, even spices is not used, and no odor is felt.

(2) Feel: In case of only raw silk, a rustle feel occurs, but in case of silk gland used as main ingredient, one feels damp (wet) and smooth.

(3) In case where the cream is applied to the affected part: In case of only raw silk, rough feel remains and sticky feel also remains; but in case of silk gland used as main ingredient, one feels smooth, and the sticky feel disappears. It is understood that the cream be absorbed damply.

The medical effects with respect to various diseases between the cream of the present invention and the comparative cream were compared.

(1) Atopic dermatitis: The cream was applied to the affected part in a normal using amount once a day. In case of the comparative cream, it took 7 to 14 days in order to appease the itch, failing to take effect for improving the condition of a disease. In case of the cream of the present invention, itch was softened immediately, and the condition of disease was improved in a week and completely recovered at least in three months. When the cream of the present invention is applied, in the procedure as described above, to a patient whose face was swollen due to the use of suprarenal body cortex hormone drug, the affected part was completely recovered in a half year.

(2) Chap: The cream was applied to the affected part in a normal using amount once a day. In case of the comparative cream, it took 15 to 30 days in order to appease the itch, and it took 1 to 3 months to improve the condition of a disease. In case of the cream of the present invention, itch was softened immediately, and the condition of disease was improved in a week.

(3) Water insect: The cream was applied to the affected part in a normal using amount once a day. In case of the comparative cream, it took 2 to 5 days in order to appease the itch, and no improvement of the condition of a disease was found. In case of the cream of the present invention, itch was softened immediately, and the condition of disease was improved in a week without peeling the affected part.

(4) Feeling stiff in shoulders: The cream was applied to the affected part in a normal using amount. In the comparative cream, it took effect about 30 minutes after being applied to the affected part, whereas in the cream of the present invention, the affected part was turned crimson immediately and the stiff and pain were softened immediately.

(5) Bruise: The cream was applied to the affected part in a normal using amount. In the comparative cream, it took effect about 30 minutes after being applied to the affected part, but the part was swollen and congested with blood with a bruise remained, whereas in the cream of the present invention, when the cream is applied into the affected part, pain in the affected part was softened immediately, and swelling, congestion with blood was gone, and no bruise occurred.

(6) Checking the bleeding: In the comparative cream, even if cream is applied to the affected part when a finger or the like is cut, it takes no effect, whereas in the cream of the present invention, the affected part is applied with the cream and bound. Then, blood was checked in a day without being stitched, and an open wound was stopped as it is.

(7) Pain of pile and bleeding: In the comparative cream, it took noeffect even if the cream is applied, whereas in the cream of the present invention, in case of bleeding piles, pain was gone in 5 minutes and bleeding was stopped soon. In case of prolapse of the anus, when the cream of the present invention is applied after took a bath, the number of times of the prolapse of the anus is reduced gradually. In case of piles, when gauze with the cream of the present invention applied is held on the affected part, the condition of a disease was improved in a month.

(8) Burn: when the comparative cream is rubbed into the deep redaffected part resulted from touching hot place, no effect was taken, but in the cream of the present invention, pain and inflammation were removed in a few minutes, and when applied immediately, no blister occurs.

(9) Nasal congestion: In case of the comparative example, no effectis taken, but when the cream of the present invention is applied to the bridge of the nose, the condition of the nose is recovered immediately.

(10) Coughing: In case of the comparative example, no effect is taken, but when the cream of the present invention is applied to the bridge of the nose, the throat, the breast, and the back, cough was stopped in about one hour.

(11) Acne: In case of the comparative example, no effect is taken, but when the cream of the present invention is rubbed thinly into the affected part in a normal using amount once a day, the condition of a disease was improved in a week, and was completely recovered in 1 to 3 months.

(12) Bedsore: Even if the comparative cream is applied to a person suffering from the bedsore stayed in bed, no effect was taken, but when the cream of the present invention is applied to the affected part, pain was softened in a day, and the wound becomes small gradually and was completely recovered in two weeks.

Those which take no effect in the comparative cream but take effect in the cream of the present invention include, other than those mentioned above, the mother's mark, pollen disease, stomatitis, wrinkles, alveolar pyorrhea, hypertrophy of prostate, and so on. From experiences for 10 years or more, those in which the silk gland is a main ingredient have the bactericidal action, anti-inflammation action (anti-itch, pain, inflammation action), anti-allergy action, hemostatic action and so on. Further, no by-effect was taken for 10 years or more.

EXAMPLE 9

Ultraviolet Preventing Effect

For assuring the ultraviolet preventing effects of the cream of the present invention and the comparative cream, the respective creams in the film thickness of 20 μm were applied to glass plates, and the ultraviolet transmittance at 300 nm was measured using a ultraviolet spectrophotometer to obtain the ultraviolet cut rate, results of which are given in Table 4. Here, the ultraviolet cut rate (%)=100 (%)–the ultraviolet transmittance (%). For the sake of comparison, in the case other than that not adding the active ingredients, the ultraviolet cut rate was likewise measured with respect to the contrast cream produced in a manner similar to the above, results of which are given in Table 4 below.

TABLE 4

| Test Cream | Ultraviolet Cut Rate |
| --- | --- |
| Present cream | 75% |
| Comparative cream | 60% |
| Contrast cream | 40% |

Advantageous Effect of the Invention

According to the present invention, the composition has no toxicity relative to the human body and has the bactericidal action, and further exhibits the great therapeutic effect for the skin diseases such as atopic dermatitis, mother's mark and the like that have been extremely difficult to be recovered completely, Further, the cosmetics of the present invention exhibits the great effect for various kinds of skin diseases, and exhibits materially conspicuous effect that cannot be attained at all in the conventional cosmetics such that the renewal of the skin surface is made active to prevent the decline of the skin, to make the skin smooth, and to make the mother's mark and pigment inconspicuous, etc.

Furthermore, the ultraviolet ray screening agent of the present invention has the excellent effect for the disease of the skin, and when used as the cosmetics, exhibits, in addition the above effect, the same anti-sunburn effect as that the ultraviolet absorbent free from toxicity is added, and besides, exhibits the function that cannot be seen at all in the conventional ultraviolet ray screening agent of this kind such that the sun burnt skin is whitened.

What is claimed is:

1. A composition having a bactericidal action which comprises an organic solvent or water extract from a silk gland containing liquid silk and/or an organic solvent or water extract from liquid silk as an active ingredient.

2. The composition according to claim 1, where the active ingredient is the extract from a mixture of one or more of a silk filament, a cocoon, a raw silk, a silk and a pupa of a silkworm in addition to the silk gland containing liquid silk and/or the liquid silk.

3. The composition according to claim 1, wherein said composition has the effect of a medicine relative to atopic derimatitis, allergy derimatitis, mother's mark, pigment, rough skin, wrinkle, acne, prickly heat, chap, burn, insect stick, dried skin, eczema, bedsore, pollen disease, water insect, ringworm, hypertrophy of prostate, pile, wart, body odor, stomatitis, alveolar pyorrhea, or catarac.

4. The composition according to claim 1, wherein said extract is water or an organic solvent extract or a concentrate in which said extract is concentrated.

5. A cosmetics having a bactericidal action wherein water or an organic solvent extract from a silk gland containing liquid silk and/or water or an organic solvent extract from liquid silk is compounded with a cosmetic base material.

6. An ultraviolet screening agent having a bactericidal action which comprises as an active ingredient an organic solvent or water extract from one or more of a silk gland containing liquid silk and a liquid silk.

7. An ultraviolet screening agent having a bactericidal action which comprises as an active ingredient an organic solvent or water extract from a silk gland containing liquid silk and/or an organic solvent or water extract from liquid silk.

* * * * *